(12) United States Patent
Swartz et al.

(10) Patent No.: US 9,821,082 B1
(45) Date of Patent: Nov. 21, 2017

(54) CONNECTED SCENT DEVICE

(71) Applicant: The Yankee Candle Company, Inc., South Deerfield, MA (US)

(72) Inventors: Melanie Swartz, Cincinnati, OH (US); Ross Millenacker, Santa Cruz, CA (US); Michael Li, Hacienda Heights, CA (US); Fan Sai Kuok, Pittsburgh, PA (US); Vishal Pallikandi, Columbia, SC (US)

(73) Assignee: The Yankee Candle Company, Inc., South Deerfield, MA (US)

( * ) Notice: Subject to any disclaimer, the term of this patent is extended or adjusted under 35 U.S.C. 154(b) by 180 days.

(21) Appl. No.: 15/011,429

(22) Filed: Jan. 29, 2016

Related U.S. Application Data

(60) Provisional application No. 62/163,294, filed on May 18, 2015, provisional application No. 62/163,303, filed on May 18, 2015.

(51) Int. Cl.
*A61L 9/03* (2006.01)
*B01F 3/04* (2006.01)
*A61L 9/12* (2006.01)

(52) U.S. Cl.
CPC ............ *A61L 9/03* (2013.01); *A61L 9/035* (2013.01); *A61L 9/12* (2013.01); *B01F 3/04085* (2013.01)

(58) Field of Classification Search
CPC ..... A61L 9/00; A61L 9/02; A61L 9/03; A61L 9/035; B01F 3/04; B01F 3/04021; B01F 3/04085

USPC ............ 239/55, 56; 261/30, 94, 95, DIG. 88
See application file for complete search history.

(56) References Cited

U.S. PATENT DOCUMENTS

| | | | |
|---|---|---|---|
| 4,836,452 A | 6/1989 | Fox | |
| 6,053,041 A | 4/2000 | Sinha | |
| 6,267,297 B1 | 7/2001 | Contadini et al. | |
| 6,802,460 B2 | 10/2004 | Hess et al. | |
| 6,827,289 B2 | 12/2004 | Filicicchia et al. | |
| 8,382,008 B1 | 2/2013 | Ricciardi et al. | |
| 9,149,031 B2 * | 10/2015 | Shi | B01F 3/04085 |
| 9,278,150 B2 | 3/2016 | Gruenbacher et al. | |
| 2006/0060990 A1 | 3/2006 | Szpekman | |
| 2007/0210182 A1 | 9/2007 | Wulteputte et al. | |
| 2009/0162253 A1 | 6/2009 | Porchia et al. | |
| 2010/0030013 A1 | 2/2010 | Brunelle et al. | |
| 2010/0044453 A1 | 2/2010 | Porchia et al. | |
| 2011/0295434 A1 | 12/2011 | Luc et al. | |
| 2012/0018037 A1 | 1/2012 | Nakagawa et al. | |

(Continued)

*Primary Examiner* — Robert A Hopkins
(74) *Attorney, Agent, or Firm* — Husch Blackwell LLP

(57) ABSTRACT

A scent dispersal device and a network for operating one or more scent dispersal devices are provided. The device can include electronics for operating a heater within the device to cause a scent cartridge within the device to disperse a scent into the surrounding environment. The device can include a top configured to turn the device on/off and control the type, strength and duration of a specific scent from a scent cartridge. The device can be equipped with sensors to identify the type of scent selected and the level of scent substance remaining in a scent cartridge. The device can be configured to interact with other scent devices via a local Wi-Fi network, where the tactile control of one device causes other devices to act in the same manner. The device or devices can further be controlled by and send information to a mobile device via a network.

20 Claims, 12 Drawing Sheets

(56) References Cited

U.S. PATENT DOCUMENTS

2013/0081541 A1     4/2013   Hasenoehrl et al.
2014/0074283 A1     3/2014   Blackburn
2016/0081181 A1     3/2016   Gruenbacher et al.

* cited by examiner

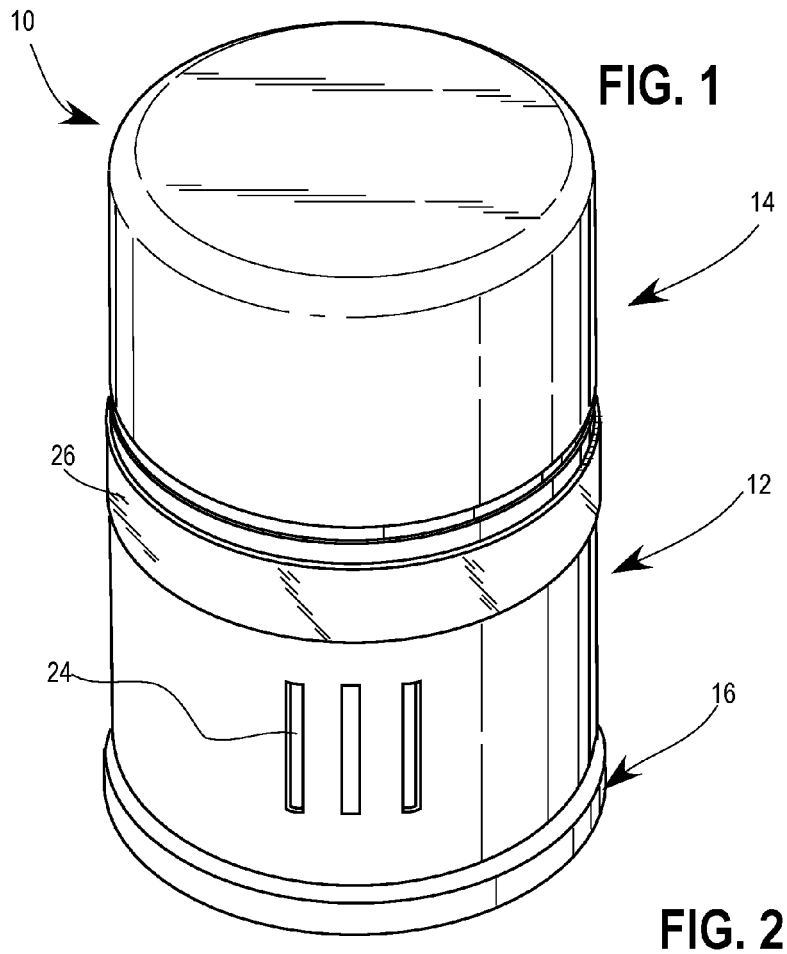
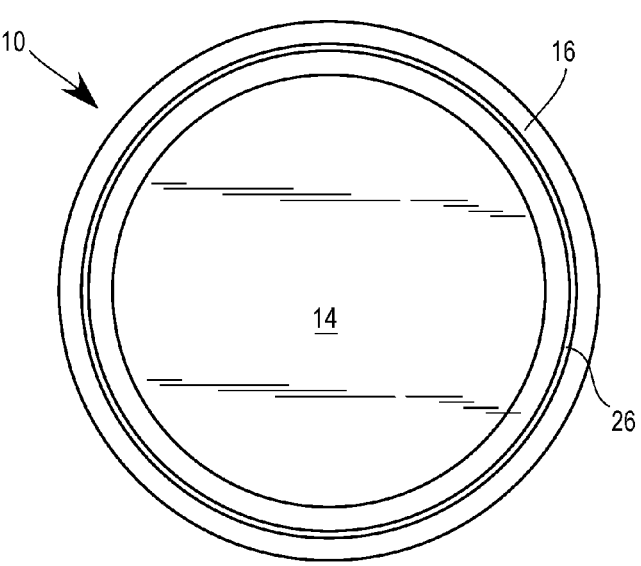

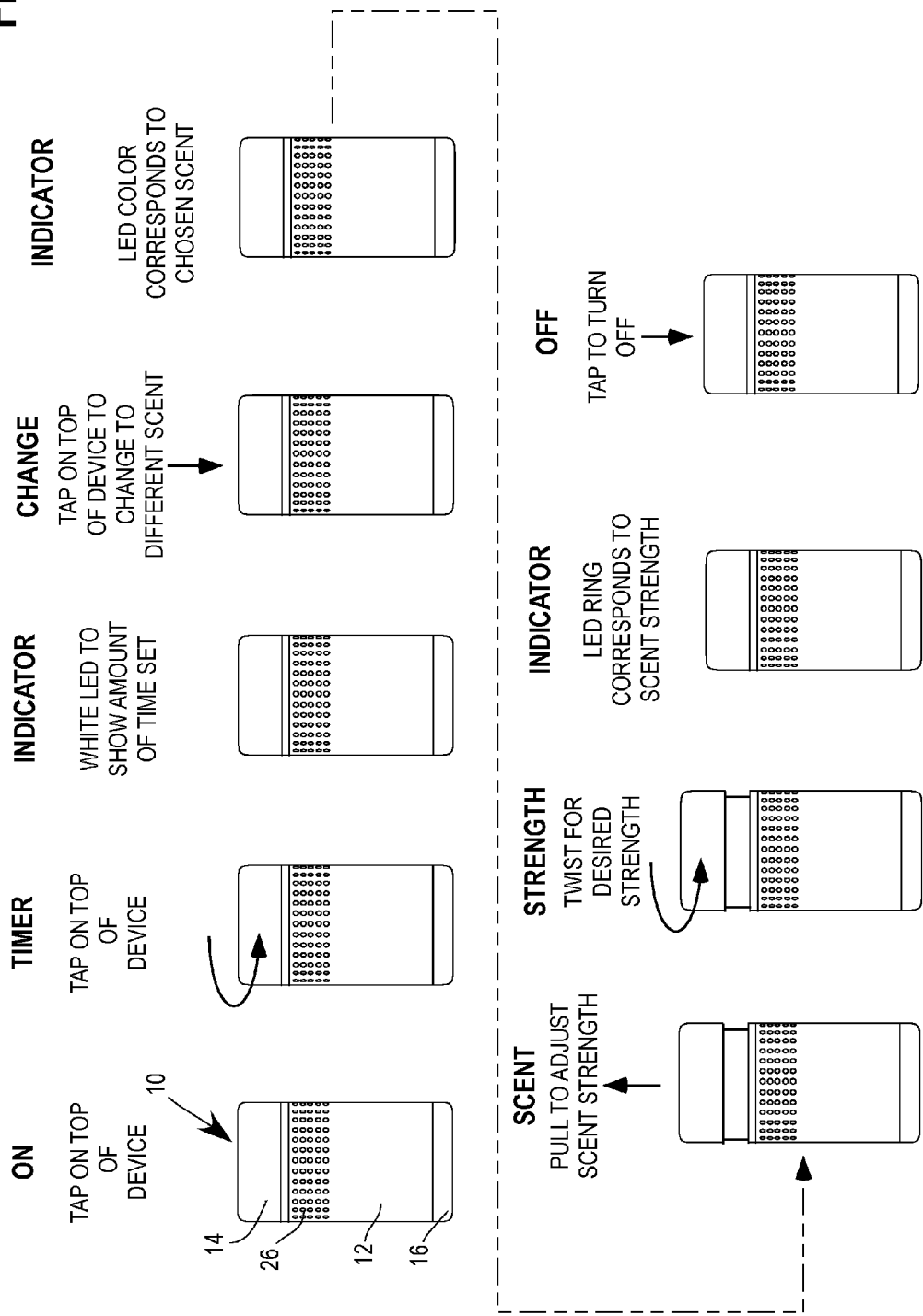

CONNECTED SCENT DEVICE

CROSS-REFERENCE TO RELATED APPLICATIONS

This Application claims priority to U.S. Provisional Patent Application Ser. No. 62/163,303, filed on May 18, 2015, to Melanie Swartz et al., entitled "Connected Scent Device," the entire disclosure of which is incorporated herein by reference, and to U.S. Provisional Patent Application Ser. No. 62/163,294, filed on May 18, 2015, to Melanie Swartz et al., entitled "Connected Scent Device," the entire disclosure of which is incorporated herein by reference.

FIELD OF THE INVENTION

The present invention relates to scent dispersion devices, and in particular, the operation and control of individual and network-connected scent dispersion devices.

BACKGROUND OF THE INVENTION

Air fresheners and scent dispensing devices that dispense or deliver scents into the surrounding environment are commonly known in the art. Many of these devices include a container or cartridge containing a scented liquid substance that is evaporated and gradually released into the air of the surrounding environment via a heater placed adjacent to the scent cartridge. Previously disclosed designs provide for scent dispensing devices containing multiple scent cartridges with different scents to allow for altering the delivered scent without changing the cartridge. Other previously disclosed designs provide for a scent dispensing device that can be controlled remotely via a remote control or mobile device.

However, many of the presently known designs for scent dispersal devices lack intuitive control and functionality desired by users of the devices. For example, many scent dispersal device designs are configured only with an on/off position. Other designs provide for remote control capabilities without sufficient tactile control functions.

There also exist designs for network-connected scent dispersal devices where a plurality of scent dispersal devices is controlled collectively. Such designs commonly control the use of the collective devices via remote sensors over a global network or allow the entire network of devices to be controlled collectively by a remote control or computer-implemented device. While such networked devices allow for the "scent conditioning" of multiple adjacent environments, they are not configured for intuitive control and functionality of each device or the collective network of devices or even a subset of the networked devices.

Accordingly a need exists for a scent dispersion device configured with intuitive control and functionality for adequately "scent-conditioning" a particular environment and meeting the needs of users. Additionally, a need exists for a network of scent dispersion devices that can be individually and/or collectively controlled by a user in an intuitive and functional manner.

SUMMARY OF THE INVENTION

The present invention is directed generally to a scent dispersion device configured for dispersing a scent into the surrounding environment. The device can include multiple scent cartridges that can each contain a scented substance, such as a scented oil or the like, that can be heated, evaporated and/or otherwise emitted into the surrounding environment by the device. To facilitate the dispersal of the scented substance, the device can include a heating component. According to one embodiment of the present invention, the heating component is a variable strength heating component so that the device can change the scent dispersal level or strength based on a user's preferences or the surrounding environment.

The device can also include several components for allowing a user to adjust settings on the device, control the device, and receive information regarding the status of the device. The device can include a timer that can allow a user to set a predetermined length of time for the device to be on and dispersing a scent. The device can further include a scent level sensor that can detect the amount of scented substance remaining in a scent cartridge so that a user can be aware of the status of a scent cartridge and alerted when a scent cartridge becomes close to expiration. The device can further include a scent type sensor that can identify the type of scented substance in a scent cartridge within the device and convey the scent type to the user. The device can further include a display element, such as an LED display, for conveying information about the device to a user.

The device can also be configured with an electronics component that can operate and control each of the functional components of the device and allow a user to control the device physically or remotely.

The device can also include one or more means for controlling the device, such as buttons, dials, touch screen and the like. According to one specific embodiment of the present invention, the scent dispersal device can be operated by a multifunctional top that enables the user manually interact with the device. To turn the device on, the user can push down on the top, which can turn on the first scent from the first loaded scent cartridge. A corresponding scent color can also be illuminated on an LED ring that extends at least partially around the top. After the device is on, several different functionalities can be accessible to the user through the multifunctional top. To set the timer, the user can twist the top in the clockwise direction to a desired time. The LED ring can illuminate and the fullness of the light ring can correspond to more time. Twisting the top counterclockwise can also allow the user to reduce the timer. To change to a different scent, the user can push down on the top again. As the user continues to push on the top, it will cycle through all of the scent cartridges loaded in the device and then turn off on a subsequent push down of the top. Each time the top is pressed, the color on the LED ring can change to correspond to the specific scent selected and the LED ring can turn off in the off position. To adjust the strength of the active scent, the user can pull up on the top and twist clockwise. Similar to the timer, the LED ring can increase in fullness as the scent strength is increased. Also similar to the timer, twisting the top counterclockwise while pulled up can reduce the scent strength. Once the timer runs out, the device can turn off until the user reactivates the device by pressing down on the top again. Several alternative means can also be used to control the device.

The present invention also relates generally to the control of a network of connected scent dispersal devices. A plurality of devices can be arranged in a local or global network, defined by proximity, space, location, user preference or other suitable characteristic. The plurality of devices can be wirelessly communicable with one another and configured for remote control. According to one embodiment, when a user adjusts the settings on one device in the network, the other devices on the network can adjust in the same manner.

The plurality of devices can also be configured for control by a remote device, such as a mobile phone or computer. The plurality of devices can also be segmented into smaller sub-networks, in which control of a device in a sub-network impacts the operation of other devices in that sub-network, but not other devices outside of the sub-network but within the overall network.

Other aspects and advantages of the present invention will be apparent from the following detailed description of the preferred embodiments and the accompanying drawing figures.

DESCRIPTION OF THE SEVERAL VIEWS OF THE DRAWING

In the accompanying drawing, which forms a part of the specification and is to be read in conjunction therewith in which like reference numerals are used to indicate like or similar parts in the various views:

FIG. 1 is a perspective view of a scent dispersal device in accordance with one embodiment of the present invention;

FIG. 2 is a top plan view of the scent dispersal device of FIG. 1;

FIG. 7 is a schematic flowchart for operating a scent dispersal device in accordance with one embodiment of the present invention;

DETAILED DESCRIPTION OF THE INVENTION

Figure 3:
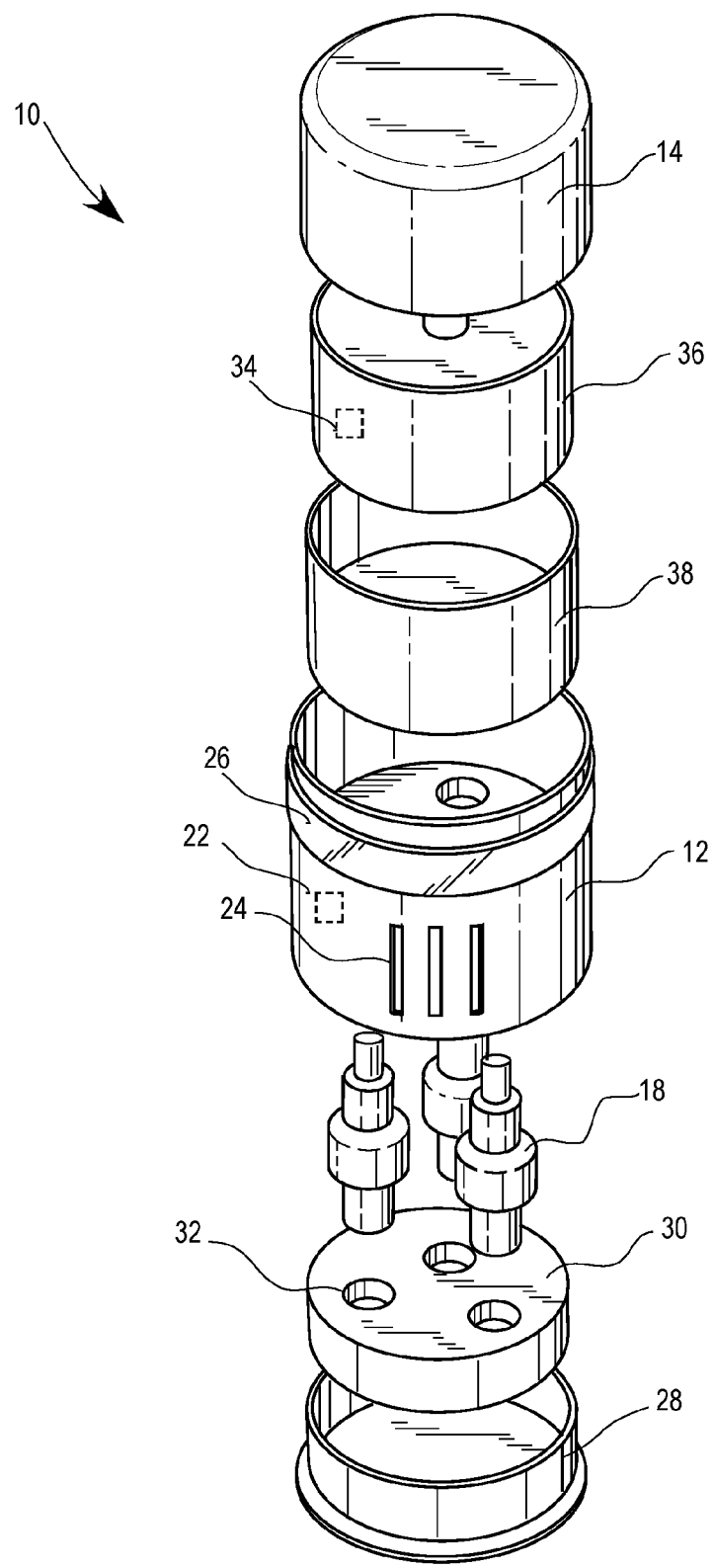
FIG. 3 is an exploded perspective view of a scent dispersal device in accordance with one embodiment of the present invention.

The invention will now be described with reference to the drawing figures, in which like reference numerals refer to like parts throughout. For purposes of clarity in illustrating the characteristics of the present invention, proportional relationships of the elements have not necessarily been maintained in the drawing figures. It will be appreciated that any dimensions included in the drawing figures are simply provided as examples and dimensions other than those provided therein are also within the scope of the invention.

The following detailed description of the invention references specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The present invention is defined by the appended claims and the description is, therefore, not to be taken in a limiting sense and shall not limit the scope of equivalents to which such claims are entitled.

Referring to the figures, the present invention is directed generally to a scent dispersal device 10. Device 10 can be configured for dispersing or emitting a scent into its surrounding environment and can be controlled via tactile controls on the device and/or network controls remotely as described in greater detail below. As shown in FIG. 1, device 10 can include a main body 12, a top 14 and a base 16. Device 10 can further include a display element 26, such as a light, an LED strip or the like for displaying certain settings, functions and/or information to a user as described in greater detail below. One or more vents 24 may be provided in main body 12.

As shown in FIG. 3, main body 12 can be configured as a housing for holding one or more scent cartridges 18, each of which can contain a scented substance 20. The figures illustrate device 10 as configured for holding three scent cartridges 18; however, device 10 can be configured for holding more or less than three scent cartridges 18 in alternative embodiments. The scent can be dispersed or emitted from device 10 by means of a heating component 22 (shown in ghost in FIG. 3) positioned within main body 12. Heating component 22 can apply heat to a scent cartridge 18 and disperse or emit scented substance 20 as a scented vapor into the surrounding environment via vents (or similar apertures). Other means for emitting scented substance 20 can alternatively be used in alternative embodiments.

Figure 4:
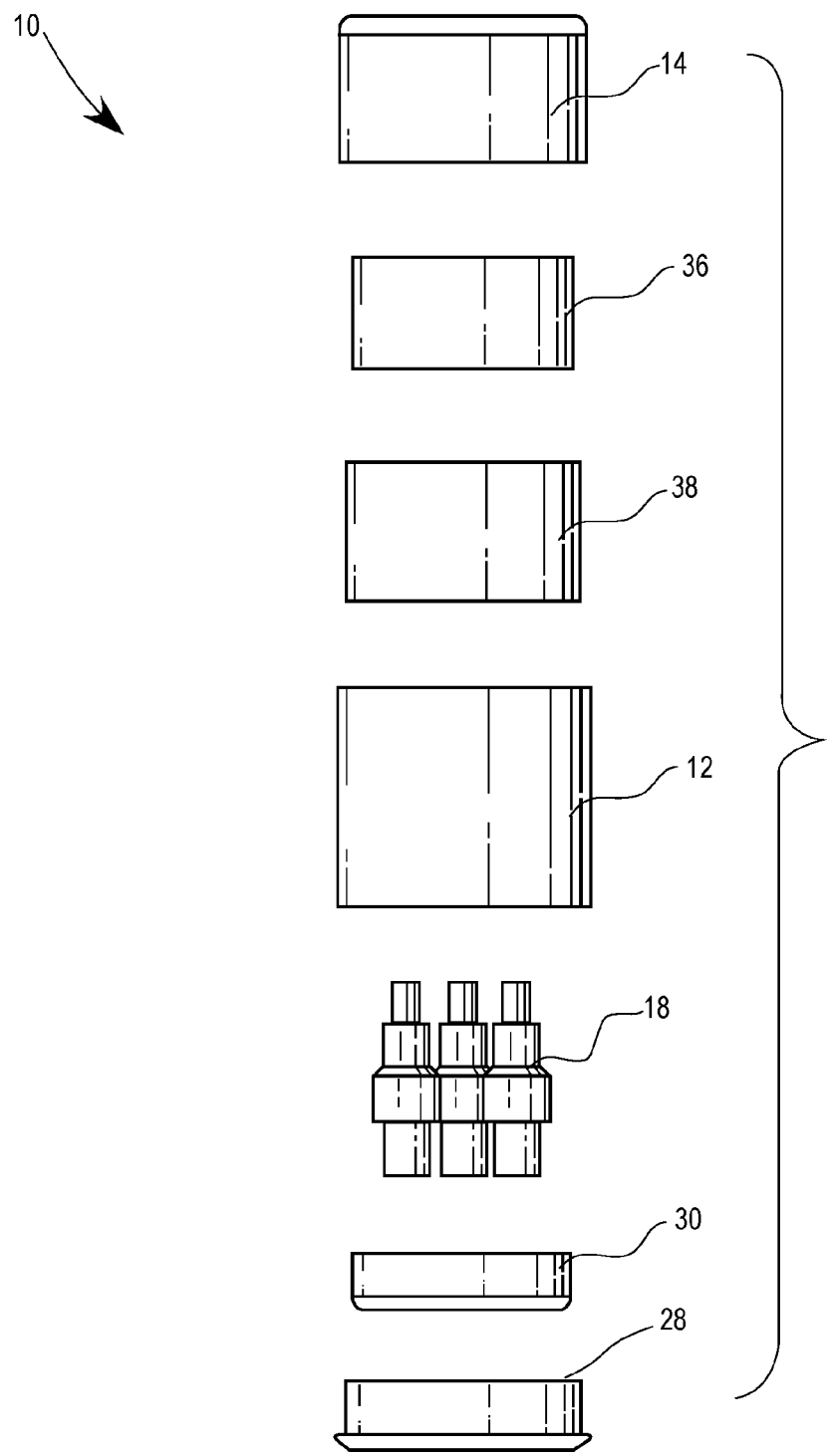
FIG. 4 is an exploded side view of a scent dispersal device in accordance with one embodiment of the present invention.
Figure 5:
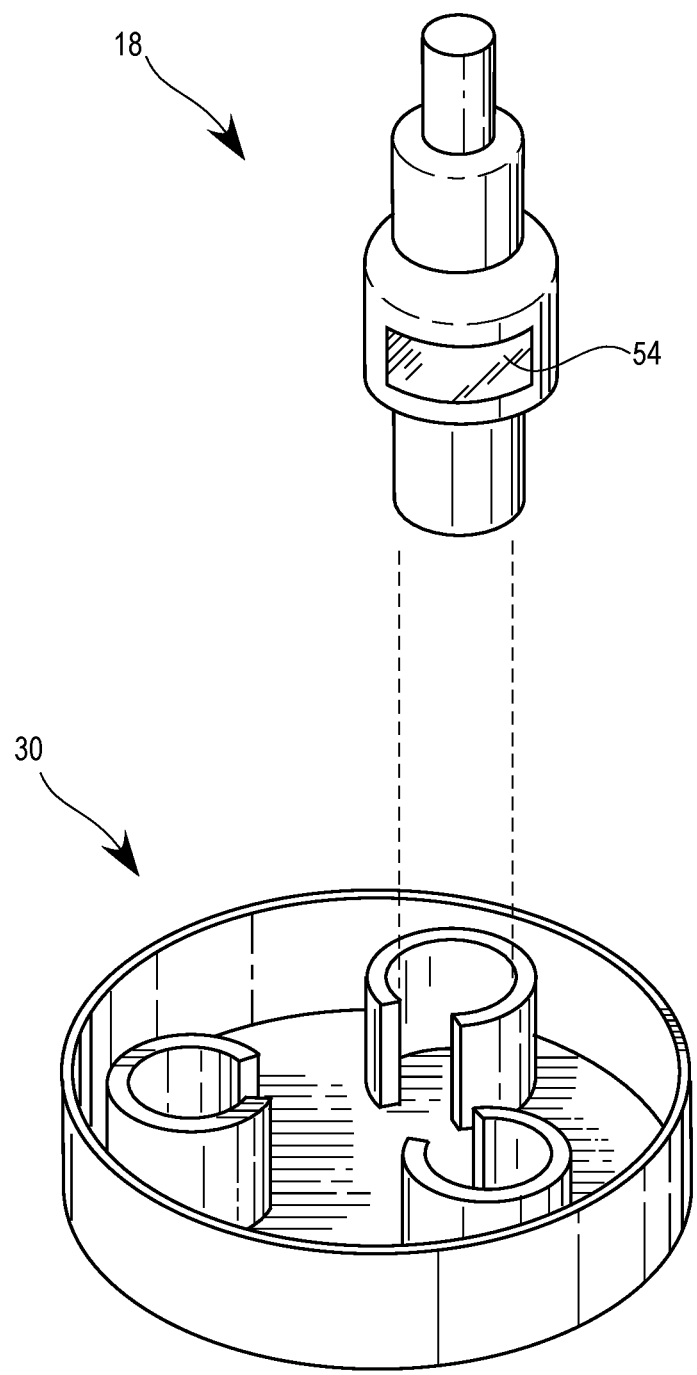
FIG. 5 is a perspective view of a scent cartridge and a mounting cup for use with a scent dispersal device in accordance with one embodiment of the present invention.

As shown in FIGS. 3 and 4, base 16 of device 10 can be a removable base 16 for allowing access to the interior housing of main body 12 according to one embodiment of the present invention. Removable base 16 can comprise a cap 28 as illustrated in FIG. 3, which can be a screw-on cap 28 having threads configured for engaging and interlocking with opposing threads on the lower end of main body 12. Alternatively, removable base 16 can comprise a cap 28 having any known suitable engagement means for selectively and removably engaging base 16 to main body 12. Removable base 16 can also include a removable mounting cup 30 having one or more slots or receptacles 32 for holding scent cartridges 18 as best shown in FIGS. 3 and 5. FIG. 5 illustrates mounting cup 30 having three slots 32 for holding three scent cartridges 18 within device 10; however, mounting cup 30 can suitably be configured to more or less than three slots 32 in alternative embodiments of the present invention. Mounting cup 30 can be integrally connected to cap 28 or can be independent from cap 28 depending on the particular embodiment of device 10. Mounting cup 30 can also be configured for being positioned within the interior housing of main body 12. When removable cap 28 is disengaged and removed from the lower end of main body 12, mounting cup 30 can be removed from the interior of main body 12 in order to provide access to the scent cartridges 18, which can allow a user to remove, check and/or replace one or more of the scent cartridges 18 positioned in slots 32 of mounting cup 30 as best shown in FIG. 3. After checking and/or replacing a scent cartridge 18, the user can then place mounting cup 30 back into the interior housing of main body 12 and re-engage cap 28 onto the lower end of main body 12.

Figure 8:
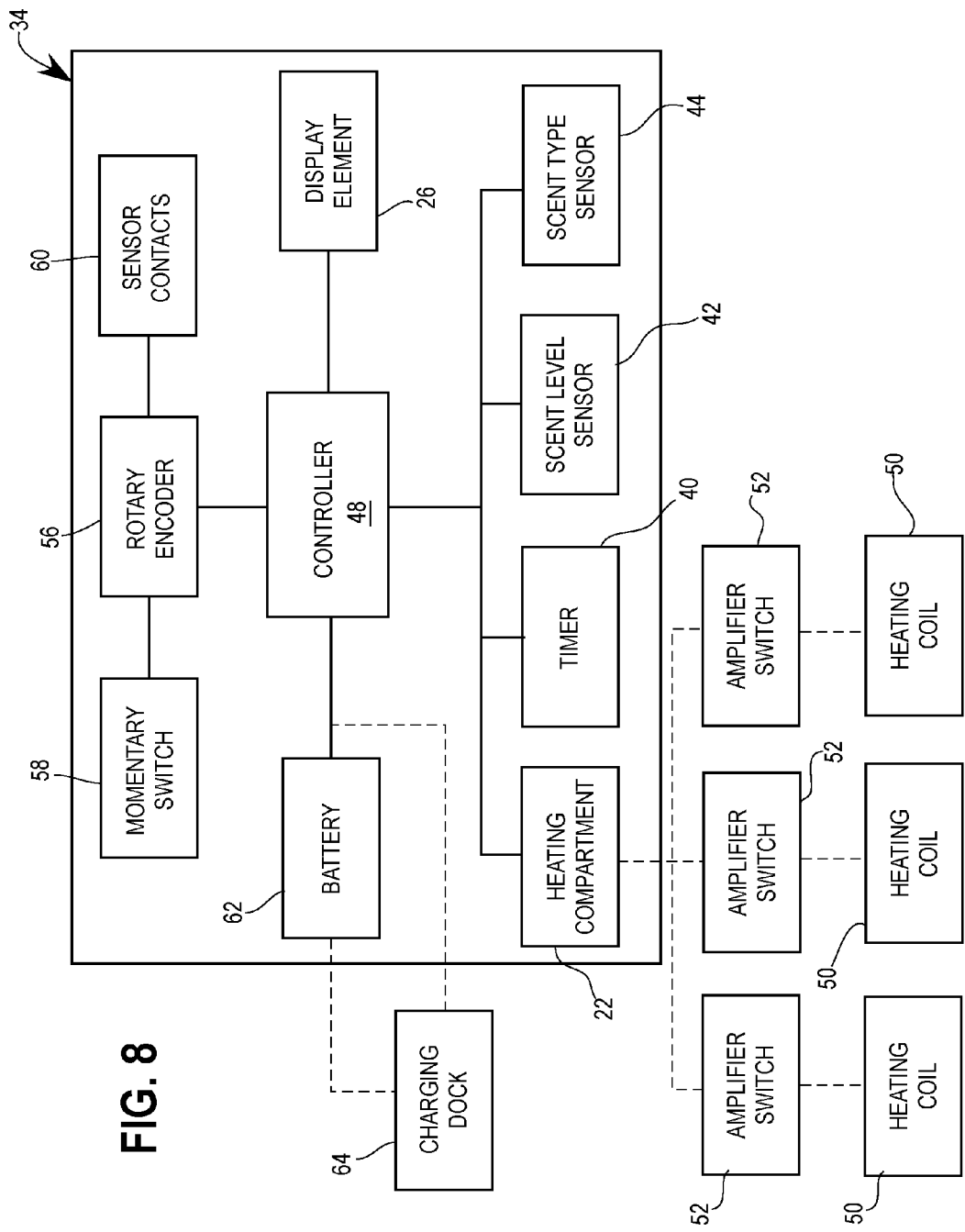
FIG. 8 is a diagrammatic view of an electronics component for a scent dispersal device in accordance with one embodiment of the present invention.

As shown in FIG. 3, device 10 can also include an electronics component 34 (shown in ghost in FIG. 3) for operating device 10 according to one embodiment of the present invention. According to one embodiment, electronics component 34 can include an electronics housing 36 and/or an electronics carriage 38 positioned in main body 12 as also shown in FIG. 3. Electronics housing 36 can be configured to hold various electronics used for controlling device 10. As schematically shown in FIG. 8, electronics component 34 can include one or more control mechanisms that can allow a user to control each of the functions of device 10 via tactile control means on device 10 as described in greater detail below. Electronics component 34 can further be configured for operating heating component 22 or other alternative means for dispensing scented substance 20 from scent cartridges 18. While the figures illustrate, and the description hereinafter describes, heating component 22 as the means for dispensing the scented substances 20, it is recognized that alternative means can be used such as ultrasonic, chemical reactions and the like. As further shown in FIG. 8, electronics component 34 can also be configured for communicating with and operating other functional components in addition to heating component 22 as described in greater detail below for improving the operation and functionality of device 10. As schematically shown in FIG. 8, such additional functional components can include, but are not limited to, display element 26, a timer 40, one or more scent level sensors 42 and one or more scent type sensors 44 according to certain embodiments of the present invention.

Figure 9:
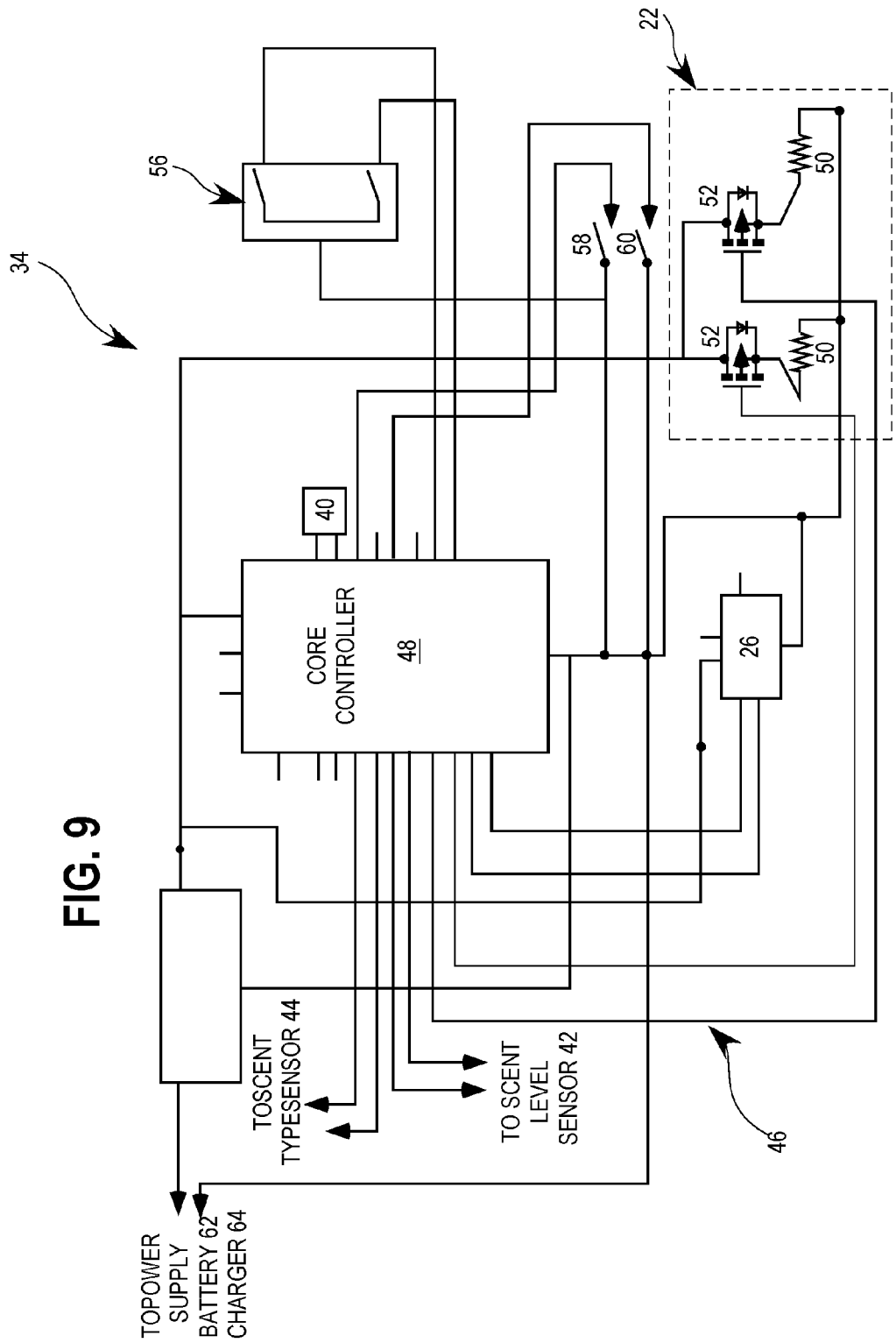
FIG. 9 is a schematic view of an electronics component for a scent dispersal device in accordance with one embodiment of the present invention.

The various components of electronics component 34 can be configured with any suitable type of general electronic circuitry 46 as schematically shown in FIG. 9 according to one embodiment of the present invention. As shown in FIGS. 8 and 9, electronics component 34 can further incorporate a core controller 48 for controlling one or more of the components comprising electronics component 34. Core controller 48 can be communicable with the tactile and/or remote control transceiver on device 10 and direct each component of electronics 34 accordingly. For example, when a user turns device 10 to an on position, controller 48 can direct heating component 22 to heat the selected scent cartridge 18. Controller 48 can also be communicable with display element 26 in order to display information about the operation of device 10 as described in greater detail below.

Heating component 22 can be configured with a heating coil 50 for each scent cartridge slot 32 in device 10 as shown in FIG. 8 according to one embodiment of the present invention. Heating component 22 can alternatively be configured with one heating coil 50 selectively positioned and configured for heating multiple scent cartridge slots 32 independently or collectively. According to one embodiment, heating component 22 comprises a single heating coil 50 for all scent cartridge slots 32 in device 10. No matter the configuration, heating element 22 can be configured for heating only one scent cartridge 18 within device 10 at a time so that a user can select between different scents at different times; however heating component 22 can also be configured for heating multiple cartridges 18 simultaneously. According to one embodiment, heating component 22 can further include an amplifying switch 52 associated with each heating coil 50 to provide device 10 with adjustable scent strength dispersal capability. Each amplifying switch 52 can control and adjust the temperature the associated heating coil 50 (from 0-100%, for example), which can control the rate that scented substance 20 is emitted from device 10. Amplifying switches 52 can comprise any suitable mechanism for amplifying and/or switching electronic signals, including but not limited to metal oxide semiconductor field-effect transistors (MOFSETs) as schematically illustrated in FIG. 9. Heating component 22 can also include a single amplifying switch 52 for multiple heating coils 50 in certain embodiments of the present invention.

When device 10 is activated by a user, controller 48 can communicate with heating element 22 to activate heating coil 50 associated with the selected cartridge slot 32. Amplifying switch 52 can control the temperature of heating coil 50 and adjust the temperature of the heating coil 50 based on the user's input. For example, when a user, via the control means, increases the scent strength, controller 48 can direct the amplifying switch 52 of the active heating coil 50 to increase in temperature, thereby increasing the scent dispersal strength. As shown in FIG. 9, controller 48 can also be configured for controlling other functional components of device 10 in various embodiments. It is also recognized that FIGS. 8 and 9 illustrate just a few possible embodiments of device 10 and electronics component 34 and several alternative configurations and means for creating an electronically communicable system known in the art can be used or incorporated in alternative embodiments of the present invention.

Device 10 can also include one or more scent level detectors or sensors 42 configured for measuring and/or detecting the amount of scent substance 16 in each scent cartridge 14. As illustrated in FIG. 8, scent level detectors 42 can be a component of electronics 34 and electronically connected to and operated via electronics 34 and/or core controller 48 according to one embodiment of the present invention. Scent level detectors 42 can be configured as optical level detectors, IR photodiode-LED pairs, and/or other known suitable detection means in various embodiments of the present invention. According to one particular embodiment of the present invention, scent level detectors 42 can measure the amount of scent substance 20 in a scent cartridge 18 by an array of photoresistors or light dependent resistors (LDRs) that can provide a Boolean value to represent whether the scent substance 20 is present at a specific level on the scent cartridge 18. Device 10 can also be configured to notify a user of device 10 when a scent cartridge 18 is low and/or the specific amount of scent substance 20 remaining in a scent cartridge 18 on device 10 itself or remotely as described in greater detail below.

Figure 6:
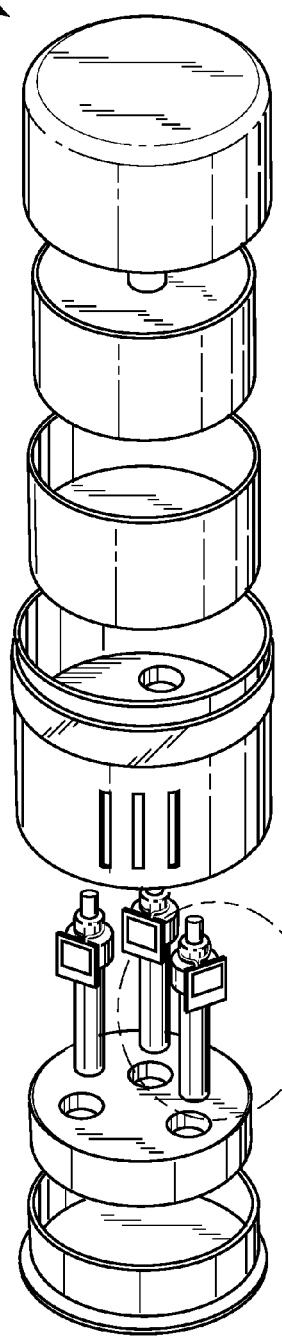
FIG. 6 is a perspective view of a scent dispersal device with scent cartridges in accordance with one embodiment of the present invention.
Figure 6A:
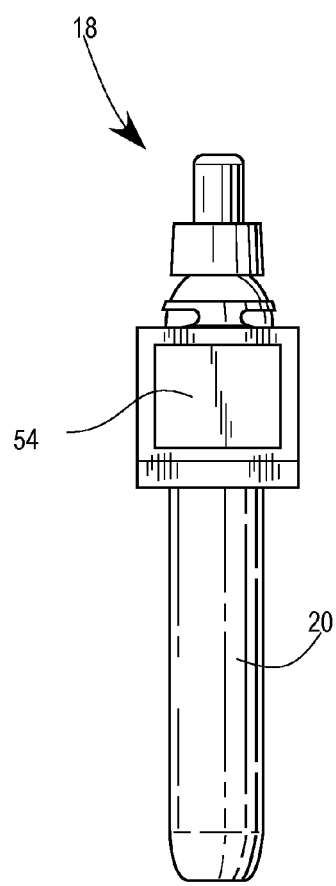
FIG. 6A is an enlarged view of one of the scent cartridges of FIG. 6.

Device 10 can also include one or more scent type detectors or sensors 44 that can be configured for identifying the type of scent substance 20 located in a scent cartridge 18, as shown in FIG. 6A, for each particular slot 32 on mounting cup 30 as illustrated in FIG. 5. As illustrated in FIG. 8, scent type detectors 44 can be a component of electronics 34 and electronically connected to and operated via electronics 34 and/or core controller 48 according to one embodiment of the present invention. According to one embodiment of the present invention, scent type detectors 44 can be configured to distinguish between difference scent substances 20 by reading identification tags 54 located on each scent cartridge 18 as illustrated in FIGS. 5 and 6A. For example, according to one embodiment, identification tags 54 can be configured as specific colored tag that can be read by visible light LED and photodiode pairs. The output of detectors 44 can then be mapped to different colors stored in detector 44, electronics 34 and/or a remote device. Any other known suitable sensing means to identify the type of scent substance 16, such as but not limited to barcode, design or color recognition sensors, can also be used in alternative embodiments of the present invention. Additionally, scent level detector 42 and scent type detector 44 can be configured as a single device in certain alternative embodiments.

Device 10 can also be configured with a timer 40 as discussed above for allowing a user to specify a time duration for device 10 to operate. As schematically shown in FIG. 9, timer 40 can be electronically provided by controller 48 or any alternative suitable and known means. When a user selects and activates timer 40 via the control means, controller 48 can keep device 10 in the on position until the desire time has elapsed, at which point controller 48 can turn device 10 to the off position. Timer 40 can also be configured so that it can be paused and/or removed once activated by overriding controls directed by the user.

As previously described, device 10 can include a display element 26 for displaying to the user the status of device 10 and the current settings of the various functional components of device 10. For example, display element 26 can indicate to a user whether the device is on or off, the type of scent currently emitting in device 10 (via sensor 44), the current strength dispersal setting of device 10 (via amplifying switch 52), the amount of time device 10 will remain in the on position (via timer 40) and/or the amount of scented substance 20 remaining in a scent cartridge 18 (via sensor 42). Display element 26 can also be configured to display several other types of settings and/or information regarding device 10.

Display element 26 can be electronically communicable with electronic component 34 and/or controller 48. According to one embodiment, display 26 is configured to receive signals from controller 48 which is electronically communicable with the other functional components of device 10, as illustrated in FIG. 8. In another embodiment, display 26 is electronically communicable directly with the functional components of device 10. Display 26 can also be configured as any suitable display mechanism. As described below, display 26 can be configured as an LED. Display 26 can also be configured as any other type of light or illumination, a screen or the like. Display 26 can also be configured to display numbers and letters or merely lights, or any combination thereof.

According to one embodiment of the present invention, display element 26 is configured as an LED strip positioned around all or part of main body 12 as illustrated in FIGS. 1 and 3. LED strip 26 can be electronically communicable with controller 48 and/or the other functional components of device 10 in order to display information about device 10 and the status of one or more of the components. For example, LED strip 26 can display different colors corresponding to the type of scent substance 20 in the scent cartridge 18 that is activated, which can be determined by scent type detector 44. LED strip 26 can also display the scent strength selected by the user by, for example, increasing the brightness and/or changing the color or shade as the user increases the scent. As described above, the adjusted scent strength can be determined by the controller 48 from communication with heating component 22 (and the active heating coil 50 and/or amplifying switch 52) and converted into a display on LED strip 26. LED strip 26 can also increase the illuminated portion of strip 26 as the scent strength is increased. LED strip 26 can similarly be used to display the time duration selected by the user when setting timer 40, notify a user when the scent substance 20 level is low in a scent cartridge 18, as well as several other communicative displays described herein.

As also described above, device 10 can be configured with one or more tactile control structures that can allow a user to physically control an individual device 10 or a plurality of networked devices 10 as described in greater detail below. The tactile control structure can be configured as buttons, dials, and similar control means electronically communicable with certain components of device 10 via electronics component 34. According to one embodiment, the tactile controls can be configured to turn device 10 on and off, select or change scent type, select or change scent strength, select or change a timer for scent dispersal, and/or other additional controls. Each function of device 10 can be controlled by a separate tactile control 50 or multiple functions can be controlled by a single tactile control 50 depending on the particular embodiment of device 10.

According to one particular embodiment of the present invention, tactile control means can be configured into top 14, which can be a multifunctional top connected to body portion 12 as illustrated in FIG. 1. As described herein, top 14 can be configured to turn device 10 on/off, shuffle through scent cartridges 18 and select a specific scent substance 20 to disperse, adjust the dispersal strength of the selected scent cartridge 18 (and scented substance 20) and/or set the timer 40 for device 10 to be on and dispersing a scent. FIG. 7 schematically illustrates the functionality of top 14 according to one embodiment of the present invention.

Top 14 can be configured for rotational motion as a dial or the like for selecting one or more functions of device 10 as shown in FIG. 7. For example, as shown in FIG. 7, a user can twist top 14 in order to adjust the scent strength and/or set the timer for device 10. Top 14 can also be configured for a push motion (such as resilient deflection similar to a button or the like) for selecting one or more addition functions of device 10. For example, as shown in FIG. 7, a user can press downward on top 14 to turn device 10 on, shuffle through the scent cartridges 18 and associated scented substances 20 and turn device 10 off. Top 14 can further be configured for a pull motion for selecting additional functions through rotational motion when top 14 is in an extended position. For example, as shown in FIG. 7, a user can pull top 14 upward and then twist top 14 in order to adjust the scent strength. FIG. 7 represents just one possible configuration for intuitive and functional control of device 10 according to one embodiment of the present invention. Several alternative configurations can be used in alternative embodiments, where the push, pull and twist motions of top 14 can be configured for different functions of device 10.

In order to enable top 14 to control functions of device 10 via a twisting or rotational motion, top 14 can be configured with a rotary encoder 56 electronically connected to core controller 48, as illustrated in FIGS. 8 and 9. When top 14 is twisted in either a clockwise or a counter-clockwise motion, the rotational motion or angular motion can be translated into an analog or digital code (such as electronic grey code pulses) through rotary encoder 56 and sent to controller 48, which can then communicate with electronic component 34, and/or the particular functional component (e.g., heating element 22 or timer 40). Alternatively, rotary encoder 56 can be directly communicable with the specific electronic component. Core controller 48 (or rotary encoder 56 directly) can also be communicable with display element 26 in order to visually display to a user the change made by the rotational motion of top 14. For example, as a user twists top 14 to adjust the time duration in which device 10 will be on (i.e., set timer 40), display element 26, such as an LED strip, can increase or decrease in brightness or size as described above. Similarly, as a user twists top 14 to adjust the scent strength, rotary encoder 56 can cause amplifying switch 52 of the heater coil 50 of the associated selected scent cartridge 18 (directly or indirectly via controller 48) to correspondingly increase or decrease the heat temperature applied to cartridge 18. At the same time, rotary encoder 56 (directly or indirectly via controller 48 can cause display element 26 to adjust in brightness, size, etc. in sync with amplifying switch 52. Additionally, according to one embodiment, rotary encoder 56 can be configured as an infinite loop encoder in order to eliminate the need to match up the position of top 14 with display element 26 and/or sync with settings on a remote control device (as described below).

To enable top 14 to control functions of device 10 via a push motion, such as for example, to turn device 10 on/off and toggle between scent cartridges 18 (and thus scent substances 20) as shown in FIG. 7, top 14 can be configured with a momentary switch 58 according to one embodiment of the present invention. As illustrated in FIG. 8, momentary switch 58 can be a part of rotary encoder 56 according to one embodiment of the present invention. When a user pushes down on top 14 (which can also press down on the stalk of rotary encoder 56), rotary encoder 56 can activate switch 58 and turn device 10 in the on position. When a user pushes down on top 14 again, momentary switch 58 (via rotary encoder 56 and or controller 48) can cause device 10 to select the next scent cartridge 18. A user can continue to press down on top 14 until all scent cartridges 18 in device 10 have been selected, at which point pressing down on top 14 can turn device 10 in the off position. Top 14 can also incorporate one or more springs (not shown) such as leaf springs to assist in providing a spring back motion.

To enable top 14 to control functions of device 10 via a pull motion, such as for example to adjust scent strength as shown in FIG. 7, main body 12 of device 10 can be configured with electronics carriage 38 (as shown in FIG. 3) that can enable top 14 to move up and down in the vertical direction. As previously described, carriage 38 can house electronics housing 36 which can also include rotary encoder 56 and one or more sensor contacts 60 (as schematically illustrated in FIGS. 8 and 9 to sense if top 60 is in a lifted position. Device 10 can also be configured with an additional carriage 38 for holding rotary encoder 56 separately from electronics housing 36 in alternative embodiments. When top 14 is in the lifted position, rotational motion of top 14 can cause a different function of device 10 to change than the function of device 10 when top is not in the lifted position. For example, as illustrated in FIG. 7, when top 14 is pulled up into the lifted position (so that sensor contact 60 are opened) and twisted or rotated, the rotational motion can be converted and sent to controller 48, which can communicate with heating component 22 as described above. In addition, as also illustrated in FIG. 7, when top 14 is not in the lifted position (so that sensor contacts 60 are not opened), the rotational motion can be converted and sent to controller 48, which can communicate with timer 40 as described above.

Device 10 can also include a battery 62 in certain embodiments of the present invention. Battery 62 can be any suitable battery commonly used in similar electronic devices and can be permanently or removably positioned in device 10. Battery 62 can be connected to electronic component 34 and configured to supply power to operate device 10 via electronics 34. Battery 62 can also enable mobility of device 10 so that it can be used in different locations within a space and transported and used between several different spaces. Alternative to battery 62 or in addition to battery 62, device 10 can be configured for use with a charging dock 64. Charging dock 66 can be a standard charging dock and can be configured to access a power source and supply power to device 10 via electronics 34 as schematically shown in FIG. 8. Charging dock 64 can also be used to charge battery 62. Any other suitable power source means can also be used with device 10 in alternative embodiments of the present invention.

Figure 10B:
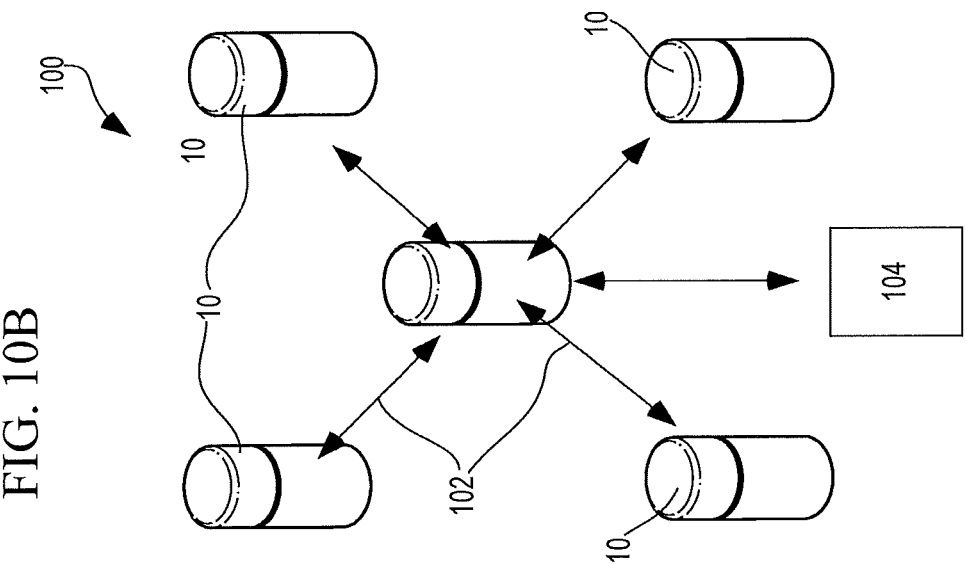
FIG. 10B is a schematic view of a local network of connected scent dispersal devices controlled by a remote in accordance with one embodiment of the present invention.
Figure 10A:
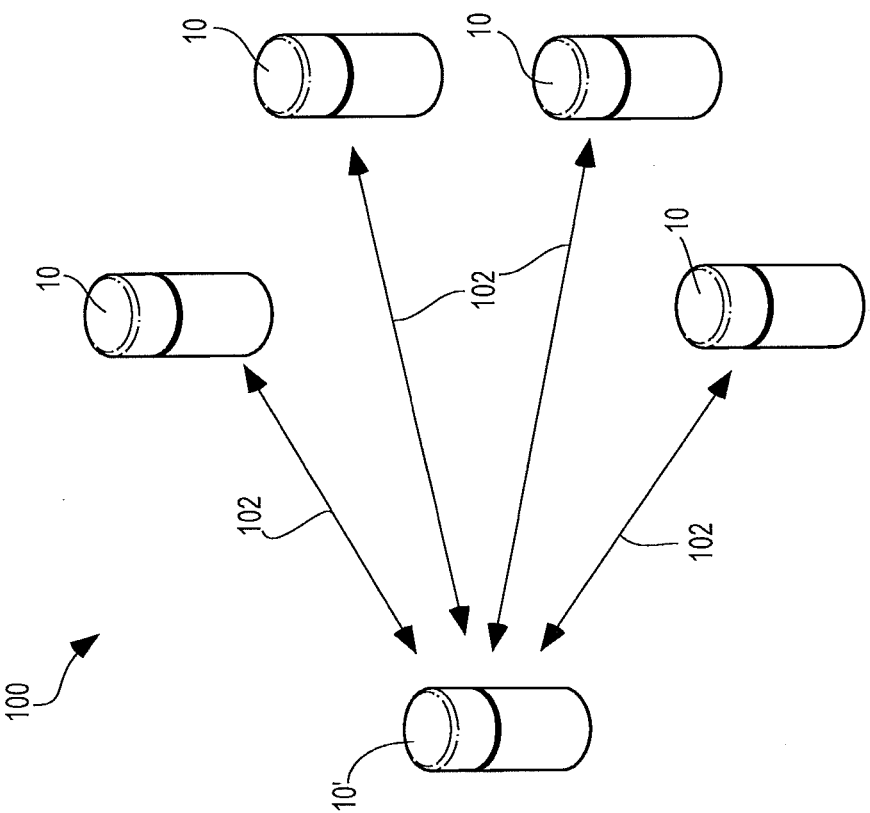
FIG. 10A is a schematic view of a local network of connected scent dispersal devices in accordance with one embodiment of the present invention.

As illustrated in FIGS. 10A and 10B, a plurality of devices 10 can be configured into a local network of devices 100 according to one embodiment of the present invention. In such an embodiment, the local network of devices 100 can be controlled collectively by the tactile control means, such as multifunctional top 14 as described above, and/or remotely as described in greater detail below. Device-to-device communication between devices 10 in the local network of devices 100 can be accomplished through a Wi-Fi network or other suitable wireless communication structure. Device-to-device communication can also be independent of an internet connection and accomplished using TCP protocols according to one embodiment of the present invention. In order to enable device-to-device communication between devices 10 in a local network 100, each controller 48 in device 10 can be configured with Wi-Fi capability or other wireless communication capabilities. The local network 100 can be configured so that each device 10 in the network 100 can have a unique identifier so that device-to-device communication is limited to devices 10 in the specific local network of devices 100.

Local network 100 can be configured so that when a user sets, changes or adjust the status or settings on one device 10 within the local network, that device 10 (by means of controller 48 and wireless communication) communicates with the remaining devices 10 in the network 100 to perform the same setting, change or adjustment. As a result, each device 10 in the network 100 can operate in a synchronized manner. As illustrated in FIG. 10A, when a user changes a setting via the tactile control means, such as top 14 in the embodiment described previously, on one device 10' in a particular local network of devices 100, that device 10' sends a wireless communication signal 102 to the other devices 10 in the network 100 instructing the other devices 10 to change the same setting. For example, when a user turns device 10' to the on position, devices 10 in the same local network 100 are also instructed to turn on. When a user changes the scent on device 10' (such as by pressing down on top 14) or increases the scent strength (such as by pulling up on top 14 and twisting clockwise), the other devices 10 in the same local network 100 also change the device scent or increase the scent strength. Local network 100 can also be configured to function with any other type of tactile control means apart from top 14 as described above.

In addition, local network 100 can be configured so that devices 10 within the local network of devices 100 can be controlled via a remote control device 104 in addition to or in place of the tactile control means on each device 10 as illustrated in FIG. 10B. In such an embodiment, remote control 104 can be configured to wirelessly communicate with each device 10 in network 100 by having wireless capability, such as Wi-Fi or other suitable wireless communication capabilities in order to send wireless signals 102 to one or all devices 10 in the local network of devices 100, as illustrated in FIG. 10B. According to one embodiment, wireless remote 104 can be a mobile or portable device or computer, such as a cellular phone, tablet, laptop or computer. In addition, local network 100 can be controlled remotely by a mobile application configured for a remote wireless device.

Figure 11:
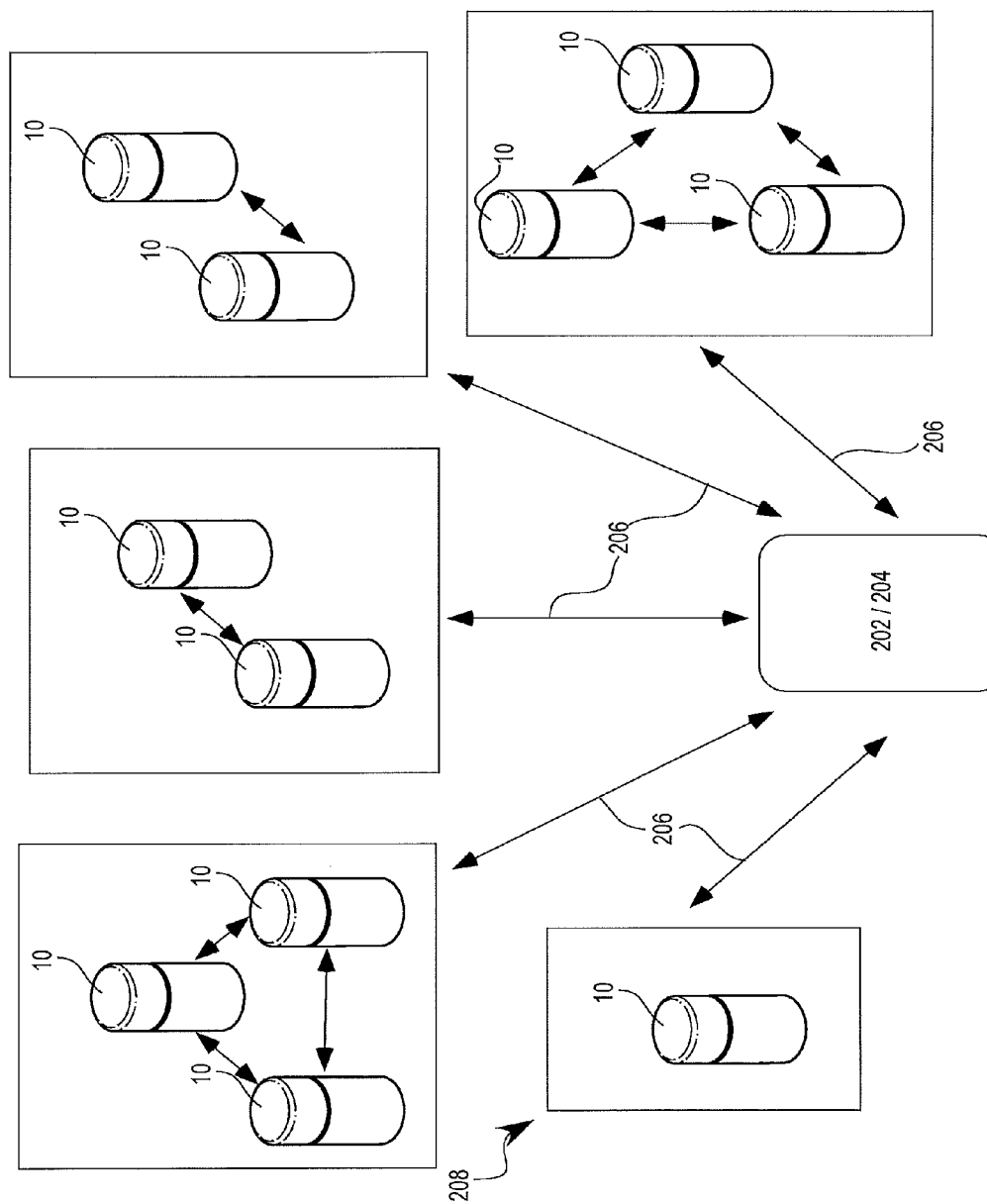
FIG. 11 is a schematic view of a global network of connected scent dispersal devices configured for remote control in accordance with one embodiment of the present invention.

As illustrated in FIG. 11, a plurality of devices 10 can be configured into a global network of devices 200 according to one embodiment. The network 200 can be configured using any combination of wireless systems and means as known in the art. Several of such systems are described in U.S. Publication No. 2015/029776 to Conroy et al., entitled "Method and System of a Network of Diffusers Including a Liquid Level Sensor," the entire disclosure of which is incorporated herein by reference. As illustrated in the embodiment in FIG. 11, each device 10 in the global network 200 can be configured for wireless communication with other devices 10 in the network 200 and other remote control devices 202, such as mobile devices, computers services and other computer implemented devices by means of Wi-Fi, internet, cellular or other wireless network communication means. Global network 200 can also be configured for control of the devices 10 within the network 200 by means of a computer, mobile and/or software application 204 as illustrated in FIG. 11. Device-to-device communication and device-to-remote device communication can be accomplished by means of wireless communication signals 206 as illustrated in FIG. 11.

Each device 10 within a global network of devices 200 can be provided with a unique identifier that allows for devices 10 to be configured into clusters of devices 208 (such as, but not limited to, a local network of devices 100). In such an embodiment, global network 200 can be used to control devices on an individual, grouped and collective basis. For example, a user can control a single device 10 on a global network 200, which can include all devices 10 within a certain environment (such as a home or office) or all devices 10 registered to an individual user, by changing the device 10 settings on remote device 202 and/or mobile app 204. A user can also control a cluster of devices 208 on a global network 200, which can include all devices 10 within a specific room or other defined space, by changing the settings for all devices 10 in the cluster 208 collectively on remote device 202 and/or mobile app 204.

Figure 12:
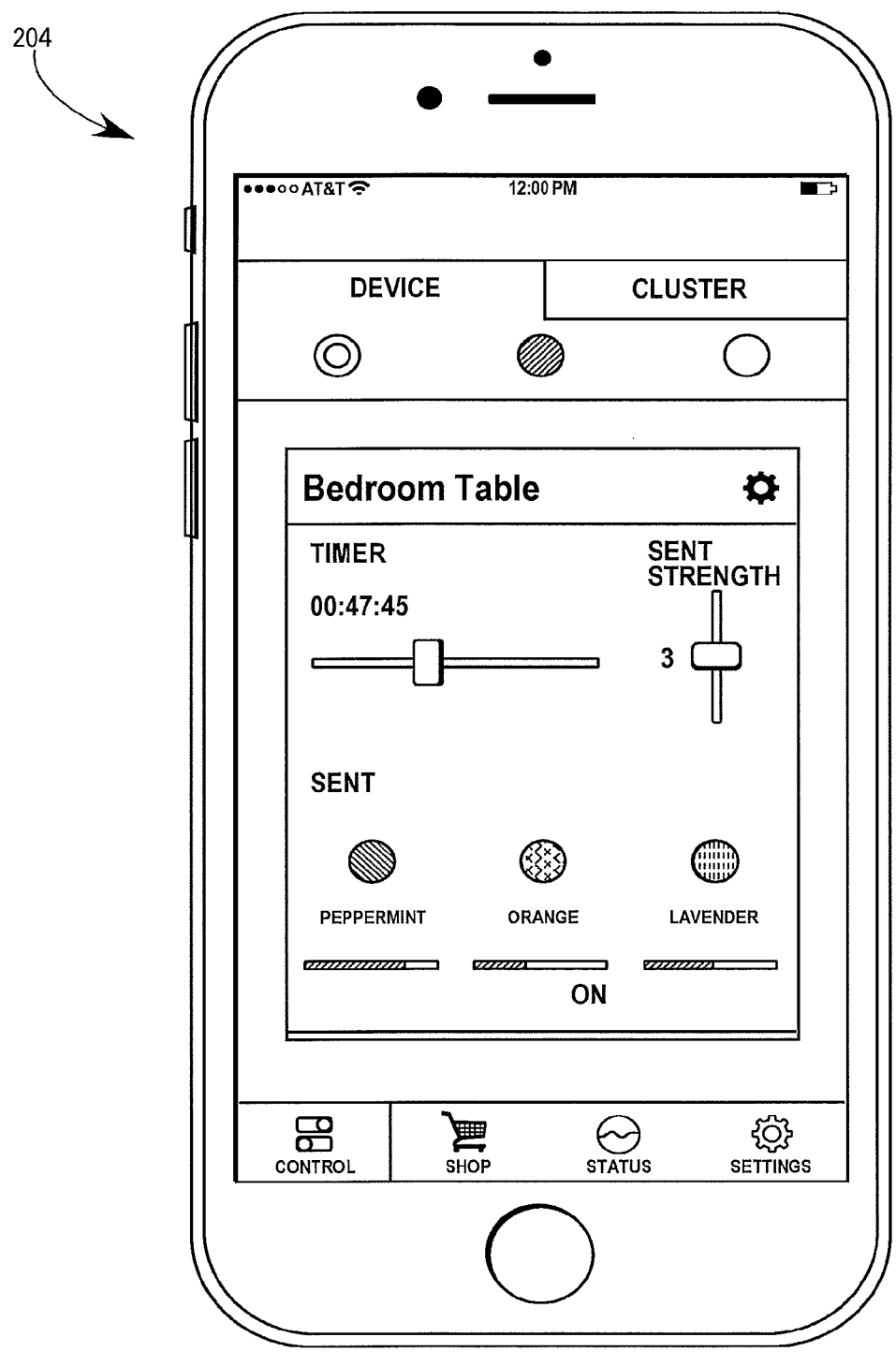
FIG. 12 is an elevation view of a mobile device and software application display for controlling a network of scent dispersal devices in accordance with one embodiment of the present invention.

Mobile app 204 can include a graphical interface, as illustrated in FIG. 12 and allow a user to control all the functions of device 10 that the user could control via the tactile control means (such as top 14) on device 10. For example, mobile app 204 could allow the user to turn device 10 on or off, select a new scent from the plurality of scent cartridges 18 in device 10, increase the strength of the scent, and/or set the timer 40 for device 10. In addition, the collective control capabilities of mobile app 204 can allow the user to control the functions of device 10 for all devices 10 within a global network 200 or a cluster of devices 208 within the global network 200.

Figure 13:
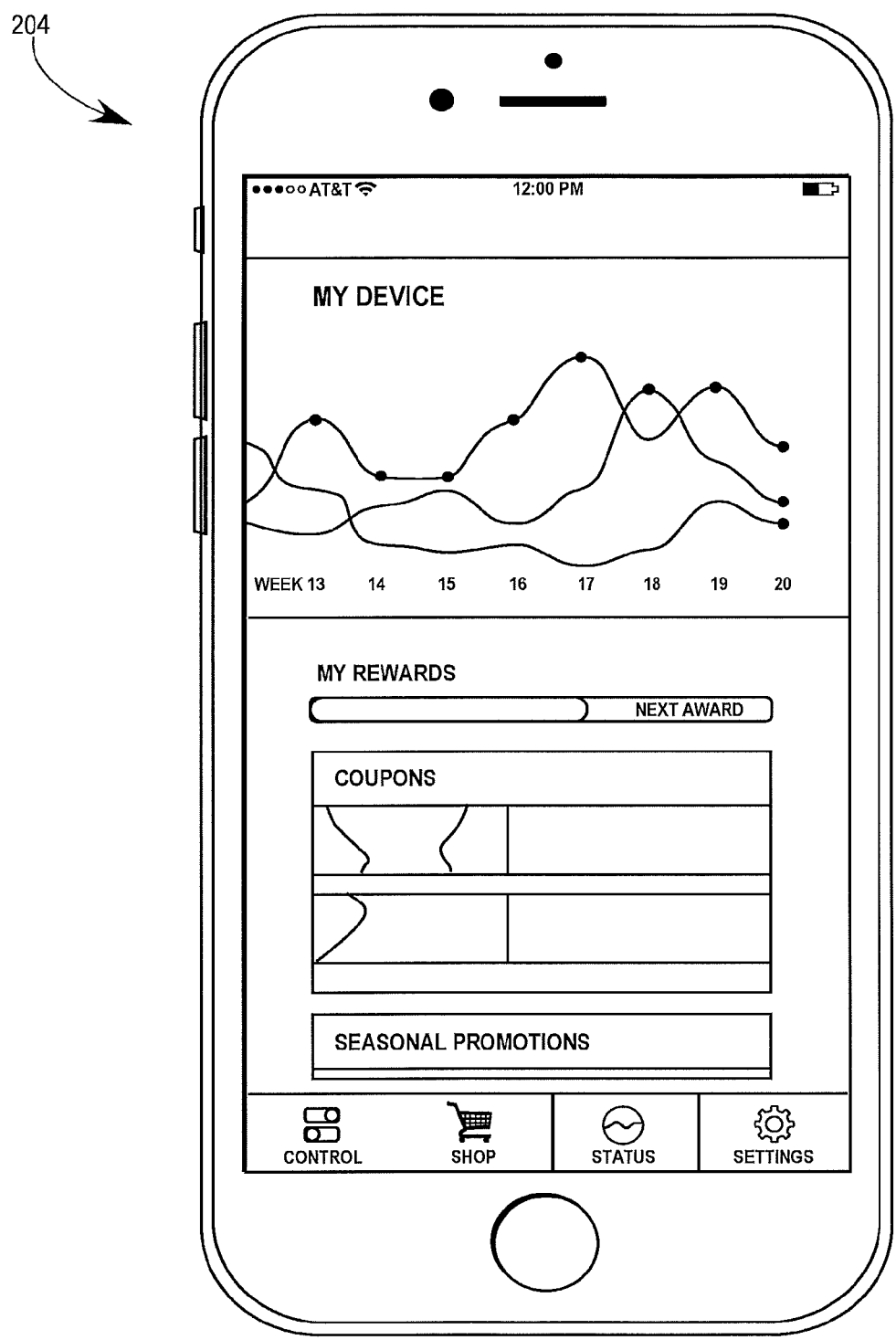
FIG. 13 is an elevation view of a mobile device and a software application display for viewing information about a network of scent dispersal devices in accordance with one embodiment of the present invention.

The mobile app 204 can also be configured to collect and display information and data from one or more devices 10 as shown in FIGS. 12 and 13. For example, app 204 can be configured to display to the user the scent level in each scent cartridge 18 as determined by scent level detector 42 as shown in FIG. 12. Similarly, app 204 can be configured to display the scent type of each scent cartridge 18 as determined by scent level 44. In addition, mobile app 204 can collect and display information regarding to a particular user's usage of each scent type, alert a user when the scent level on a cartridge 18 is getting low, promotions and means to purchase new scent cartridges 18, as shown in FIG. 13. The mobile app 204 can further collect and send this information to third parties.

From the foregoing, it will be seen that this invention is one well adapted to attain all the ends and objects hereinabove set forth together with other advantages which are obvious and which are inherent to the structure. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A scent dispersal device for dispersing a scent into a surrounding environment, comprising:
   a main body having an interior configured for housing one or more scent cartridges;
   a removable base removably connected to said main body and configured for allowing access to said interior of said main body;
   an emitting component configured for causing one of said scent cartridges to emit said scent from said one cartridge into said surrounding environment; and
   a top connected to said main body and configured enabling a user to control said device.

2. The scent dispersal device of claim 1, wherein said top is configured for rotational movement relative said main body and is configured for vertical movement relative to said main body, and wherein said rotational movement and said vertical movement of said top can selectively control one or more settings of said device.

3. The scent dispersal device of claim 2, wherein said device includes an electronics component for identifying and tracking said rotational and said vertical movement of said top for selectively controlling said settings of said device.

4. The scent dispersal device of claim 3, wherein said electronics component includes a rotary encoder for tracking said rotational movement of said top.

5. The scent dispersal device of claim 4, wherein said electronics component includes a momentary switch for tracking said vertical movement of said top and at least one sensor contact for tracking a vertical position of said top relative to said main body.

6. The scent dispersal device of claim 3, further comprising a display component electronically communicable with said electronics component and configured for selectively displaying a change in said settings of said device.

7. The scent dispersal device of claim 6, wherein said display component comprises an LED strip spanning at least a portion of said main body.

8. The scent dispersal device of claim 1, further comprising a scent level sensor for sensing a level of a scent substance located in one of said scent cartridges.

9. The scent dispersal device of claim 8, wherein said scent level sensor comprises one or more IR photodiode-LED pairs.

10. The scent dispersal device of claim 1, further comprising a scent type sensor for sensing a type of said scent in one of said scent cartridges.

11. The scent dispersal device of claim 10, wherein said scent type sensor comprises one or more IR photodiode-LED pairs for sensing an identification component on said scent cartridge.

12. The scent dispersal device of claim 1, further comprising an electronics component configured for wirelessly communicating with one or more additional scent dispersal devices.

13. A scent dispersal device for dispersing a scent into a surrounding environment, said scent dispersal device comprising:
   a main body having an interior configured for housing one or more scent cartridges;
   a removable base removably connected to said main body and configured for allowing access to said interior of said main body;
   a top connected to said main body and configured for enabling a user to control said device;
   an emitting component configured for causing one of said scent cartridges to emit said scent from said one cartridge into said surrounding environment at a selectively variable strength;
   a display element configured for displaying information about said device to said user;
   a scent level sensor for sensing an amount of a scent substance in said one of said scent cartridges;
   a scent type sensor for sensing a type of said scent substance in said one of said scent cartridges; and
   an electronics component electronically communicable with said top, said emitting component, said display element, said scent level sensor and said scent type sensor;
   wherein said top is configured for rotational movement and vertical movement relative to said main body portion;
   wherein said rotational movement and said vertical movement of said top can selectively control one or more settings of said device;
   wherein said electronics component is configured for identifying said rotational movement and said vertical movement and is further configured for controlling at least one of said emitting component, display element and scent type sensor based on said movement.

14. The scent dispersal device of claim 13, wherein said device is configured for allowing said user to change said scent dispersed from said device by vertical movement of said top.

15. The scent dispersal device of claim 13, wherein said device is configured for allowing said user to set a time duration for said device to disperse said scent into said surrounding environment by rotational movement of said top.

16. The scent dispersal device of claim 13, wherein said device is configured for allowing said user to adjust said selectively variable strength of said emission of said scent by rotational movement of said top.

17. The scent dispersal device of claim 13, wherein said device is wirelessly communicable with one or more similar scent dispersal devices.

18. A network one or more scent dispersal devices, each one of said one or more scent dispersal devices comprising:
   a main body having an interior configured for housing one or more scent cartridges;
   a top connected to said main body and configured for enabling a user to control said device;
   an emitting component configured for causing one of said scent cartridges to emit said scent from said one or more scent cartridges into said surrounding environment at a selectively variable strength;
   a display element configured for displaying information about said device to said user; and
   an electronics component electronically communicable with said top and said emitting component;
   wherein said electronics component is configured for wireless communication with each one of said one or more scent dispersal devices in said network;
   wherein said network is configured for synchronous control by a user.

19. The network of claim 18, wherein said network is configured for allowing said user to synchronously control all of said one or more scent dispersal devices in said network by said top of one of said one or more scent dispersal devices in said network.

20. The network of claim 18, wherein said network is configured for allowing said user to control said devices in said network by a remote device wirelessly connected to said network.

* * * * *